United States Patent
Pfander et al.

(10) Patent No.: US 6,405,068 B1
(45) Date of Patent: Jun. 11, 2002

(54) DIAGNOSTIC IMAGING IN RELATION TO ARTHRITIC CONDITIONS

(75) Inventors: Andreas Pfander; Jan Petersen, both of Horsholm (DK)

(73) Assignee: Osteometer Meditech A/S, Horsholm (DK)

(*) Notice: Subject to any disclaimer, the term of this patent is extended or adjusted under 35 U.S.C. 154(b) by 0 days.

(21) Appl. No.: 09/366,569

(22) Filed: Aug. 4, 1999

Related U.S. Application Data (63) Continuation of application No. PCT/EP98/00540, filed on Feb. 2, 1998.

(30) Foreign Application Priority Data

Feb. 4, 1997 (GB) .............................. 9702202

(51) Int. Cl.[7] ................................ A61B 5/05
(52) U.S. Cl. ................ 600/407; 600/425; 600/426; 378/53; 378/62; 378/98; 378/54; 378/55; 378/56
(58) Field of Search ................ 600/407, 425, 600/436; 378/53, 54, 55, 56, 58, 62, 98; 128/899

(56) References Cited

U.S. PATENT DOCUMENTS

| | | | |
|---|---|---|---|
| 3,639,764 A | * | 2/1972 | Olson et al. ............ 378/193 |
| 4,721,112 A | * | 1/1988 | Hirano et al. ............ 128/659 |
| 4,829,549 A | | 5/1989 | Vogel et al. |
| 4,956,859 A | | 9/1990 | Lanza et al. |
| 4,973,846 A | | 11/1990 | Lanza et al. |
| 5,319,206 A | | 6/1994 | Lee et al. |
| 5,381,014 A | | 1/1995 | Jeromin et al. |
| 5,563,421 A | | 10/1996 | Lee et al. |
| 5,673,298 A | * | 9/1997 | Mazess ............ 378/54 |

FOREIGN PATENT DOCUMENTS

| | | |
|---|---|---|
| EP | 0 228 785 | 7/1987 |
| EP | 0 648 467 | 4/1995 |
| WO | 79-00779 | 10/1979 |
| WO | 88-00697 | 1/1988 |
| WO | 96/35372 | 11/1996 |

* cited by examiner

*Primary Examiner*—Marvin M. Lateef
*Assistant Examiner*—Jeoyuh Lin
(74) *Attorney, Agent, or Firm*—Pillsbury Winthrop LLP (57) ABSTRACT

Methods of imaging bone provide diagnostic information relating to arthritic conditions by comparing the relative bone density in areas closer to and further removed from a potentially arthritic joint with similar relative bone densities indicative of arthritic condition such as rheumatoid arthritis. The joint may be metacarpal, finger or toe joint.

12 Claims, 12 Drawing Sheets

DIAGNOSTIC IMAGING IN RELATION TO ARTHRITIC CONDITIONS

This application continuation of PCT/EP98/00540 filed Feb. 2, 1998.

The present invention relates to methods and apparatus useful as an aid to the diagnosis of arthritic conditions including rheumatoid arthritis, osteoarthritis and gout.

There are numerous (possibly over 100) different types of arthritis of which the three listed above are the most common.

At present, arthritic conditions are diagnosed essentially only when damage to one or more joints has progressed to a sufficiently severe stage that it is diagnosable on the basis of symptoms, but diagnosis may be confirmed by changes visually identifiable on X-ray. For instance, in confirming diagnosis of rheumatoid arthritis affecting the joints of the hand, doctors will look at X-rays of the bones of the hand immediately behind the joint to identify an area of reduced bone density behind the end plate of the bone involved in the joint which shows up as a light spot in the bone on a typical X-ray photograph. However, this feature is only identifiable once the bone density has fallen by about one third of what it would normally be.

Rheumatoid arthritis is often difficult to diagnose because the symptoms usually start gradually and the course of the disease varies from person to person. Physicians diagnose rheumatoid arthritis based on the overall pattern of symptoms, medical history, physical examination and laboratory tests including a blood test. The blood test may help determine if rheumatoid factor is present, an abnormal substance found in the blood of about eighty percent of adults with rheumatoid arthritis. However, the presence or absence of rheumatoid factor does not in itself indicate that the patient has rheumatoid arthritis. Early in the disease, people may notice general fatigue, soreness, stiffness and aching. Pain usually occurs in the same joints on both sides of the body and will usually start in the hands or feet. Rheumatoid arthritis can also affect wrists, elbows, shoulders, neck, knees, hips and ankles. Other symptoms include lumps called rheumatoid nodules under the skin in areas that receive pressure such as the backs of the elbows.

Earlier positive diagnosis of rheumatoid arthritis would assist in studying the disease and in treating its symptoms.

Osteoarthritis or degenerative joint disease is one of the oldest recognised and most common types of arthritis. It is characterised by the breakdown of the joint cartilage causing bone to rub against bone and hence pain and loss of movement. Once again, osteoarthritis is presently diagnosable by only symptoms and at the stage where changes in the joint can be visually identified. However, most people over sixty have osteoarthritis on X-ray but only one third of these have actual symptoms.

Gout is a disease that causes sudden, severe attacks of pain, tenderness, redness, warmth and swelling in some joints. It usually affects one joint at a time. The pain and swelling are caused by uric acid crystals that deposit in a joint. Such attacks may be followed by the development of deforming deposits in the joint.

To allow earlier diagnosis of rheumatoid arthritis and/or differentiation between rheumatoid arthritis and osteoarthritis or gout, and/or monitoring of the progress of a said condition the present invention provides a method for diagnostic imaging comprising producing-one or more images of at least a portion of a bone involved in a potentially arthritic joint based on data reflective of bone density, e.g. an X-ray absorbence image of said bone, said image or images individually or in aggregate including a first region of said bone sufficiently close to said joint to be affected by an arthritic condition and a second region of said bone at least a part of which is spaced from said first region, and providing a read-out of bone density of said first region of said bone relative to the bone density of said second region or of each said bone density separately, and making a comparison of said read-out with at least one value for said read-out indicative of a said arthritic condition, e.g. of rheumatoid arthritis.

The bone densities may each be measured in absolute terms. Alternatively, the values of each region may only be related to the absolute bone density. Preferably, the bone is a bone of the hand, more particularly a finger bone or metacarpal bone, or a bone of the foot, more particularly a toe bone or metatarsal.

Preferably, the second region at least includes a portion spaced from the first region by at least 10 mm, more preferably by at least 20 mm.

The second region is preferably further from the joint than the first region but it is within the scope of the invention for the second region and the first region to be spaced along a line running across the bone so that they are approximately equidistant from the joint.

Preferably, a read out is provided of the bone density along a line axial of said bone extending from said joint.

The region of the bone close to the joint is preferably immediately behind the end plate of the bone. One should ideally measure in an area extending as close to the end of the bone as possible without getting into the soft tissue region or a region where two bones overlap.

Suitably, the read out is of a ratio between the measurements at said first and second regions, e.g. the ratio between a region of local bone density increase immediately adjacent the joint and a bone density found at around the centre of the bone.

However, generally, the bone density (or related value) for the region removed from the joint does not have to be made at the centre of the bone. Any point that may be consistently found in different patients, or on separate occasions in the same patient, may serve. Similarly, the measurement near the joint need not be at the point maximally affected but could be at any reproducible fixed point, e.g. a certain distance from the end plate.

Preferably, one or both of the regions of bone used, preferably both, are ones in which the bone has a high trabecular content. Optionally, both are close to or at the axial centre of the bone.

In an alternative aspect, the invention includes obtaining data relevant to the diagnosis or monitoring of an arthritic condition, comprising measuring the bone density of a portion of a bone involved in a potentially arthritic joint, said portion being adjacent the end of the bone involved in said joint, and comparing said bone density measurement with at least one value for said measurement indicative of a rheumatoid arthritis condition.

The bone density is preferably but not necessarily measured by X-ray absorbence.

For use in either aspect of the invention, there is provided apparatus for use in diagnostic X-ray imaging comprising an X-ray source, means for supporting and fixing in position at least a portion of a hand or foot for imaging using said X-ray source, and a two-dimensional pixel array X-ray detector for producing image data indicative of bone density in said hand or foot or portion thereof. Preferably, the supporting means is adapted to support a finger of the hand or a toe of the foot for imaging and to hold the same still during exposure.

The invention will be further described and illustrated with reference to the accompanying drawings in which.

Figure 1:
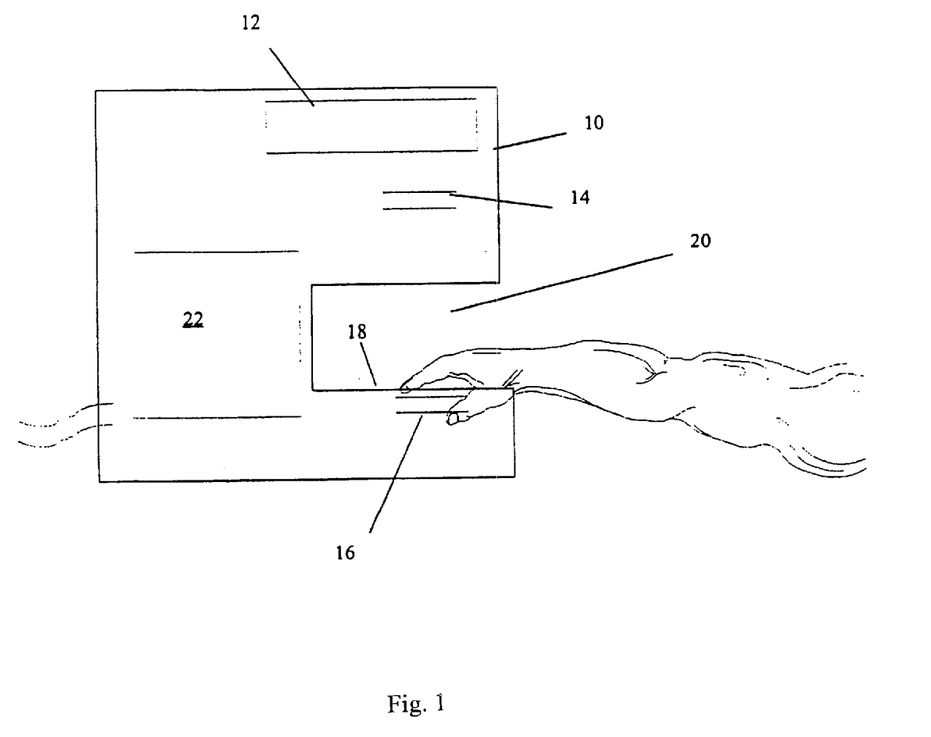
FIG. 1 shows in schematic side elevation apparatus according to the invention.

As shown in FIG. 1, apparatus according to the invention may comprise a housing 10 containing an X-ray tube 12 emitting X-rays in a downwards direction optionally through a filter 14 towards a CCD sensor 16 positioned below a finger receiving surface 18 at the bottom of an aperture 20 in the housing. The apparatus could also be used for imaging the foot. The output from the CCD sensor is processed by electronics schematically indicated at 22 to produce the required output in distal form to a suitable computer and display screen.

The X-ray tube may be designed for dual energy output. Dual energy X-ray tubes may be made either to produce the required energy X-rays and lower energy X-rays sequentially or to produce them simultaneously. Either system may be employed in this apparatus. Preferably however, the X-ray tube provides a first exposure at a higher X-ray tube voltage such as 55 kV through the filter 14 which is present to remove most of the unwanted lower energy radiation. A second exposure is then made of a lower X-ray tube voltage, e.g. 35 kV with the filter removed or replaced by an appropriate filter suited to the desired low energy range.

The data from each exposure is collected separately and is processed together to remove the influence of soft tissue in a known manner by a process of image subtraction.

The CCD sensor will comprise a scintillator layer serving to produce a visible light output in response to receiving X-rays from the X-ray tube backed by a fibre optic connection to a two dimensional CCD array. Such CCD sensors are known for use in dental X-ray devices and may be used in the illustrated apparatus without modification. The output from the CCD sensor is passed through the electronics, for instance to a personal computer, for image processing and measurement. The electronics also serve to drive the X-ray tube to make the required exposures. The size of the pixels of the CCD sensor may preferably be such as to produce a spatial resolution of 30 to 40 pm or better. Variants on this type of CCD detector that have no scintillator or fibre optic plate or which have only a scintillator with no fibre optic plate may be used.

The X-ray tube suitably produces a short (e.g. up to 500 ms, more especially 40 to 200 ms) pulse of X-rays at about 1 to 7 mA, e.g. 5 to 7 mA. Suitably, the imaging area of the CCD chip is about 2.5×3 cm which is big enough to image a single joint of the finger or the phalanxes. The exposure time need only be about half a second or less depending upon the X-ray tube used. Means may be provided for fixating the patient's finger to avoid patient movement between exposures. This may involve the provision of special cushions to allow the imaging of bent fingers or alternatively supports for the finger so that the finger is imaged from the side rather than from the top. This would make it possible to image a bent finger without the use of extra cushioning.

A solenoid or alternative device may be provided to move the filter(s) in and out of the X-ray beam as required.

In place of the CCD sensor one may instead employ an amorphous silicon or amorphous selenium imaging sensor known in the art. Such sensors employ arrays of thin film transistors which respond to inputs of charge produced in response to the receipt of X-rays either directly captured and converted into electronic data or captured and converted in scintillator layer providing a light output which is in turn captured by photodiodes linked to the thin film transistors. Devices of this sort are described in U.S. Pat. Nos. 5,319,206, 5,381,014 and 5,563,421.

Figure 2:
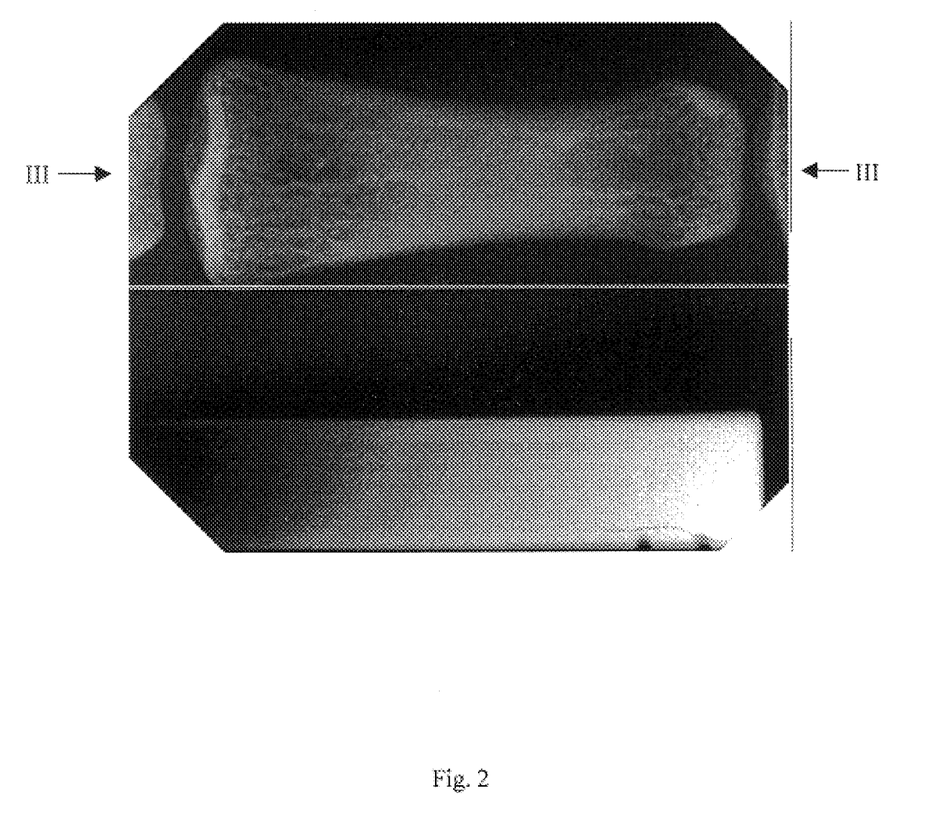
FIG. 2 shows a typical X-ray image produced using the apparatus of FIG. 1.
Figure 3:
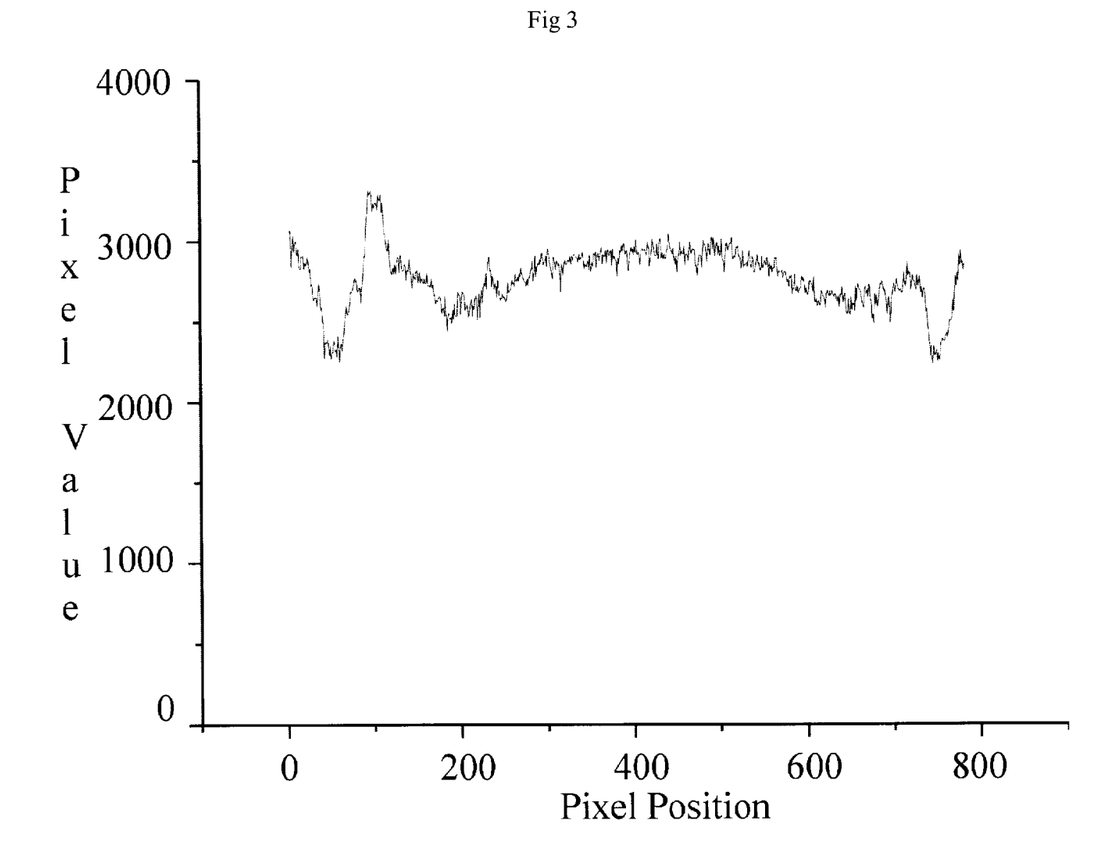
FIG. 3 shows the variation of measured bone density in arbitrary bone density units along the line III—III marked in FIG. 2.
Figure 5:
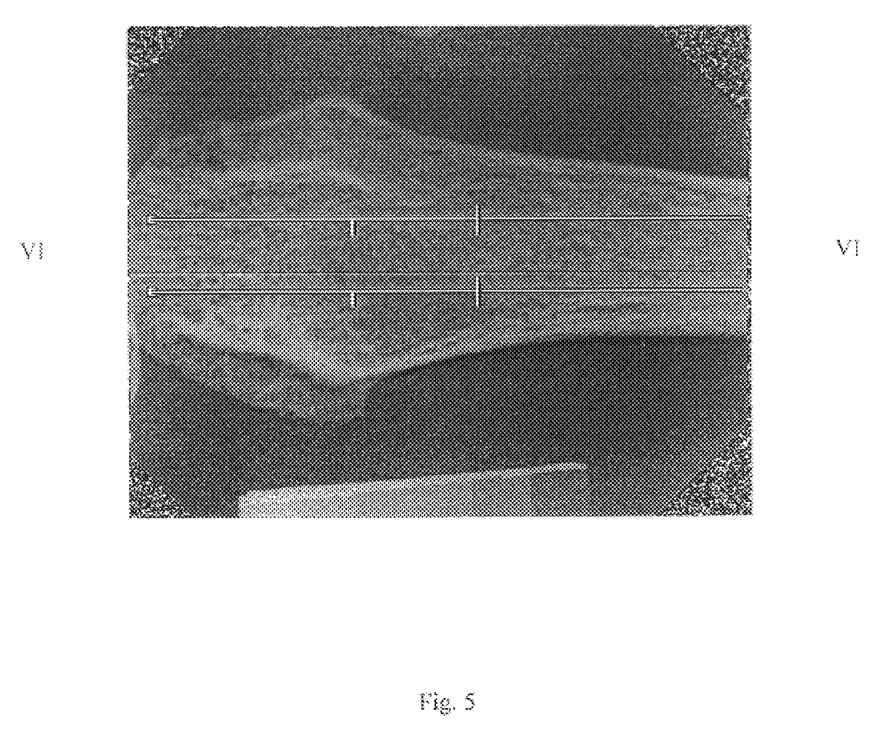
FIG. 5 shows a dual energy X-ray image of a metacarpal bone.
Figure 6:
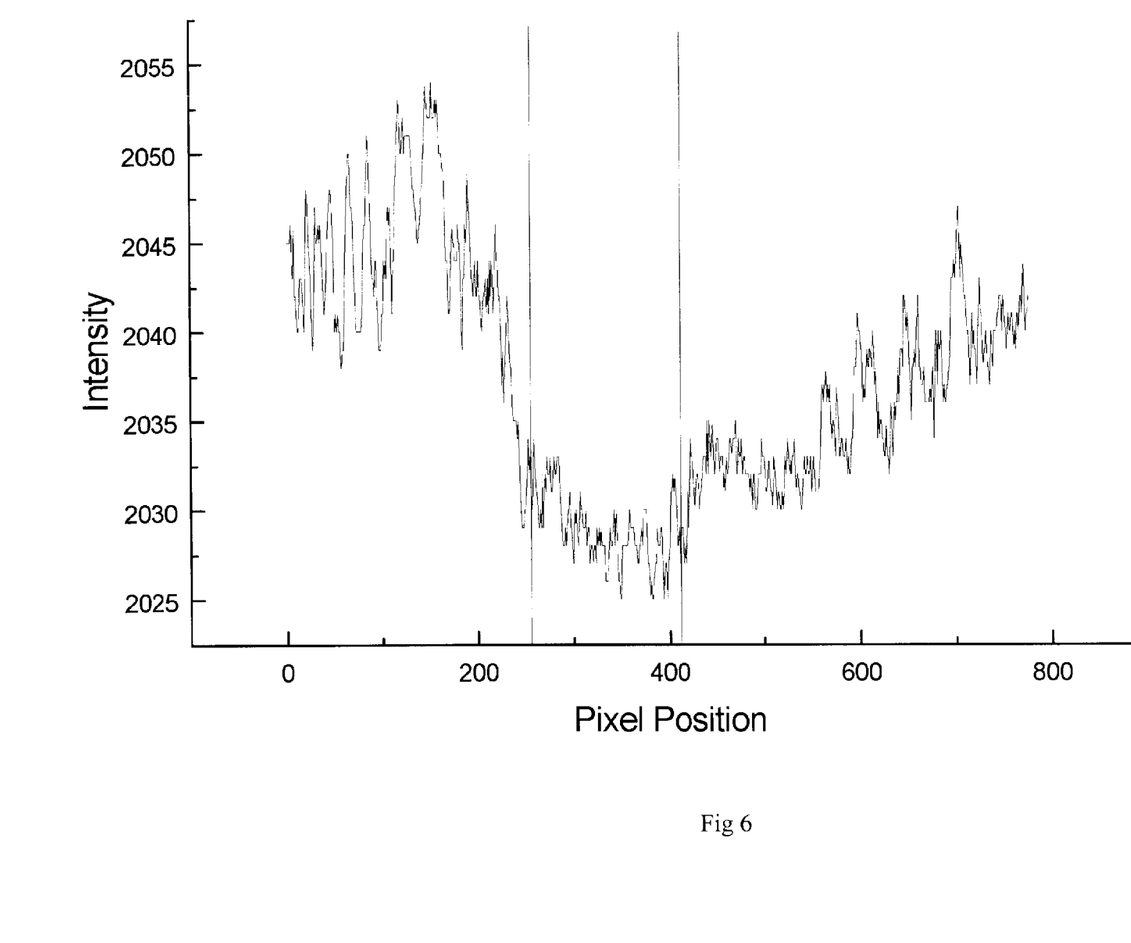
FIG. 6 shows a plot of the bone density measured along the band between the lines marked VI—VI in FIG. 5.
Figure 7:
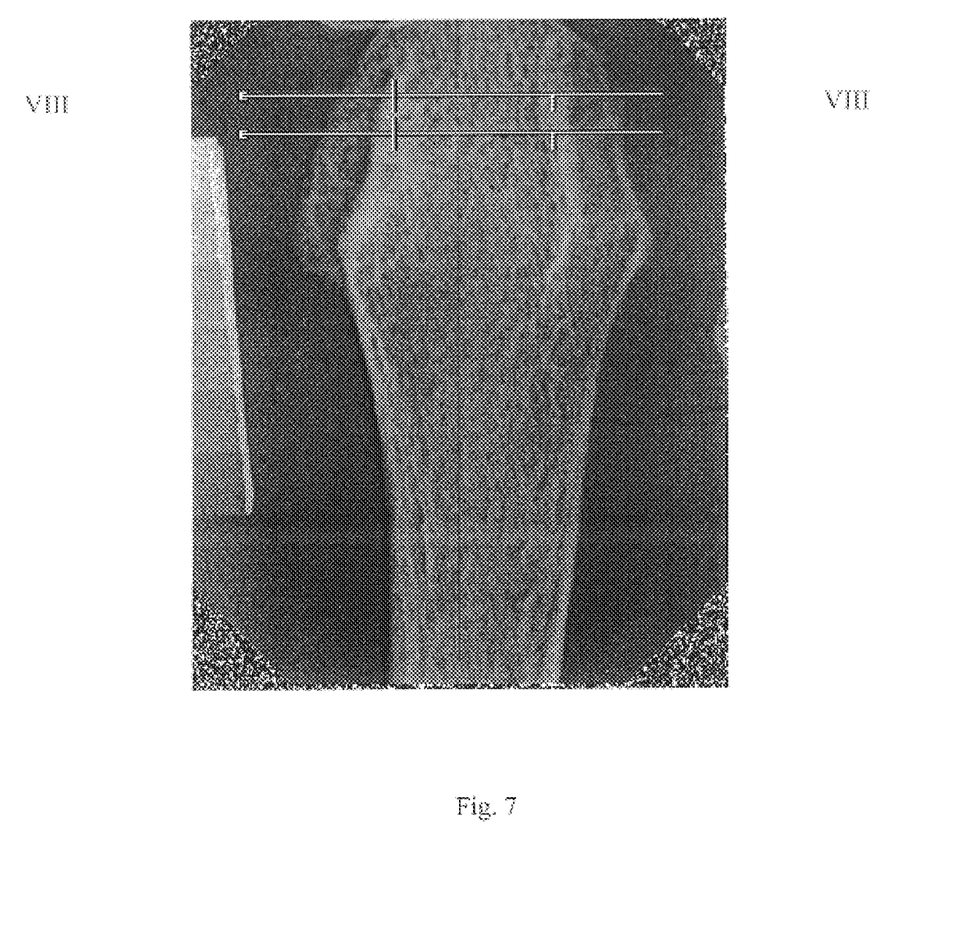
FIG. 7 shows the image of FIG. 5 marked with lines VIII—VIII.

FIG. 2 is an image from a single X-ray energy scan of a bone mounted on plastics. The bone is a human finger bone. From a pair of higher and lower energy exposures as described, images similar to the one shown in FIGS. 5, 7, 9 and 11 may be formed. The density of the image is read along the line III—III in FIG. 2 or the band VI—VI in FIG. 5 to derive the variation in bone density axially along the bone as shown in FIGS. 3 and 6. Such a scan allows comparison of the bone density immediately behind the end plate of the bone with that in its central axial region. Variations in the bone density immediately behind the end plate which are far too small to be identifiable visually may thus be detected, with the bone acting as its own control and calibration for the apparatus.

Instead of a dual energy X-ray source, one may employ a single energy source, either simply relying on the contribution from soft tissue being constant over the scanned area within acceptable limits or using a calibration wedge set next to the bone. optionally, an anti-scatter grid may be included between the scintillator layer of the detector and the patient's hand or foot as known in the art.

Figure 4:
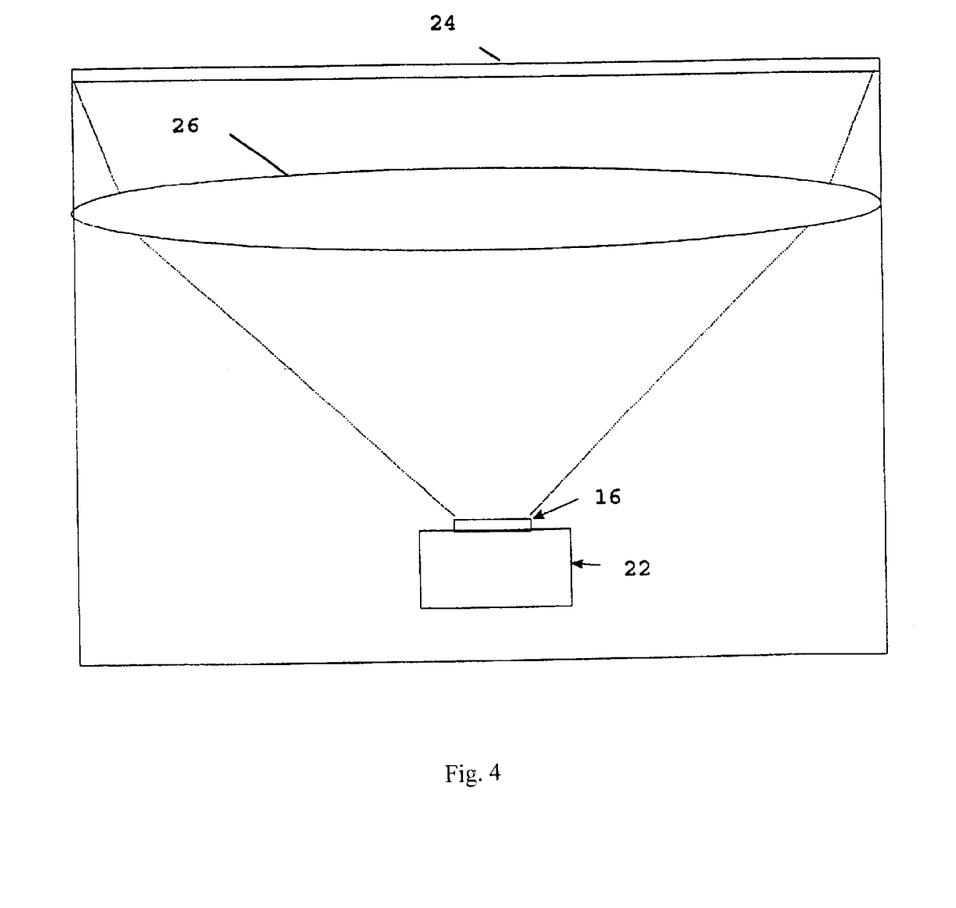
FIG. 4 shows a further form of apparatus according to the invention in schematic side elevation.

The apparatus shown in FIG. 4 is adapted to provide an image of the whole hand (or at least the whole hand excluding the thumb) and comprises a scintillation screen 24 located below an X-ray source (not shown). The hand or foot to be imaged is placed over the scintillation screen and subjected to X-ray. X-rays passing through the hand or foot produce a light output in the scintillation screen 24 which is collected by a lens 26 below the screen and focused on to a CCD sensor 16 to produce electrical signals picked up by electronics 22. in place of this arrangement however, one could use a full size CCD in place of the scintillation screen and lens, or an amorphous silicon detector, a point scan detector scanned in two dimensions or a line scan detector, e.g. a line scanner using a diode line array or a CCD line array, or any other imaging system. An image intensifier may be used.

There may be a filter positioned between the X-ray source and the body part being imaged and a filter changer allowing a choice of filters to be used.

Whilst according to the invention one may choose freely the regions of bone for use in comparing bone density closer to and further away from the site of involvement of the bone in a joint liable to be affected by rheumatoid arthritis, optimal results will be obtained by careful selection of regions of interest for comparison. The best regions of interest to use will depend upon the bone and joint in question. The metacarpal bones, especially that of the middle finger, are often among the first to be affected in rheumatoid arthritis and may be a particularly suitable choice of bone on which to practice the invention.

Figure 9:
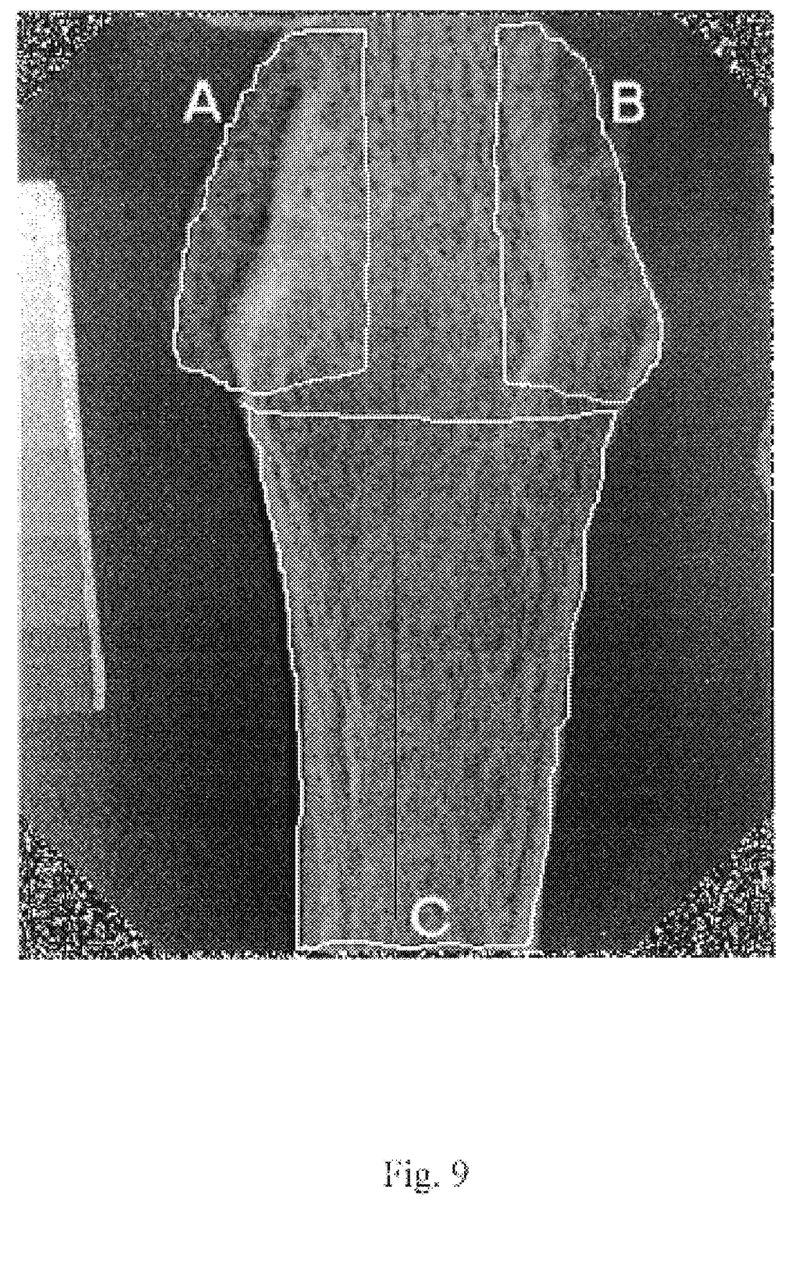
FIG. 9 shows the image shown in FIG. 5 with regions of interest marked.
Figure 11:
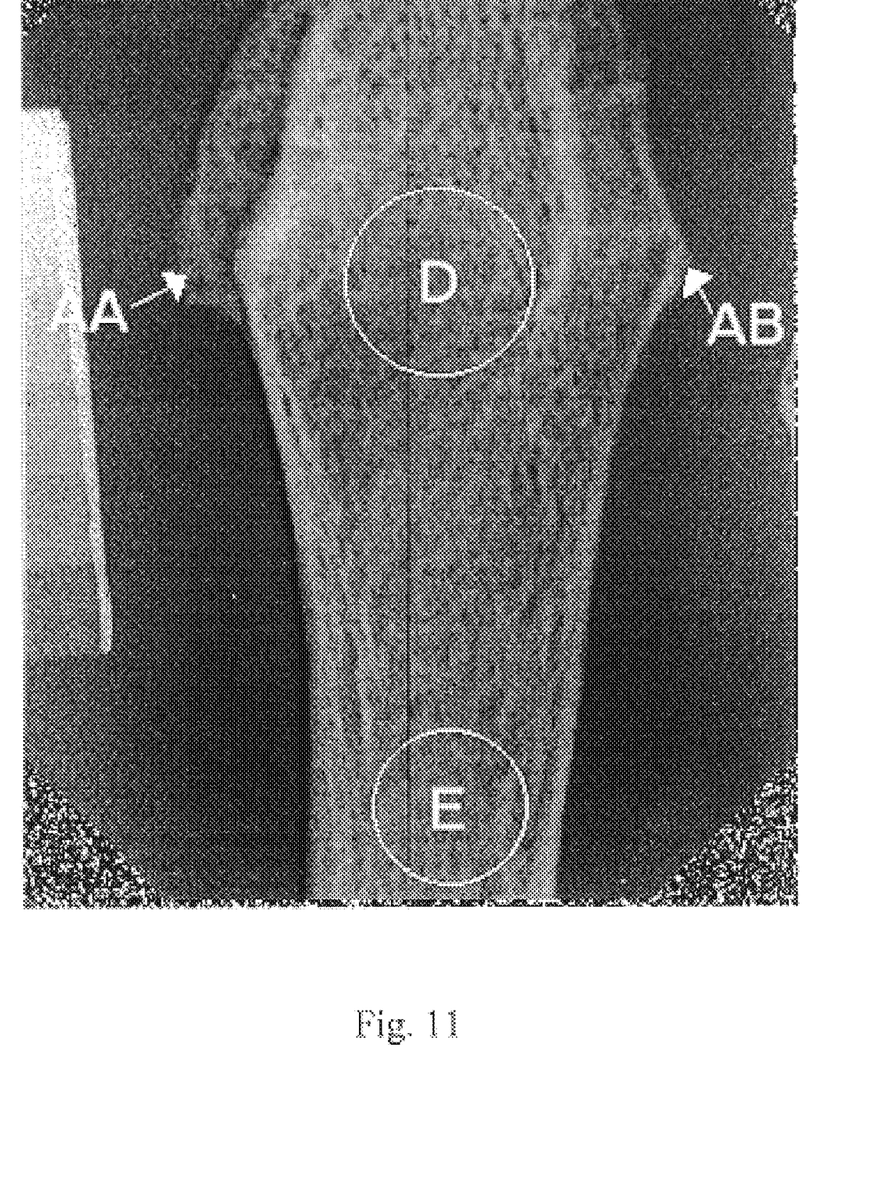
FIG. 11 shows the image of FIG. 9 with alternative regions of interest marked.

FIGS. 9 and 11 illustrate suitable regions of interest in the distal part of such a middle metacarpal bone, those shown in FIG. 9 being the most preferred.

In FIG. 9, a region of interest ("Area 23" in FIG. 10), defined at the distal extremity of the bone, takes in lateral areas A, B of the bone as seen in the image and excludes a central corridor separating the lateral areas. Said lateral areas extend from the distal end of the bone in the axial direction up to and just past the point of maximum width of the bone. The excluded central corridor is of approximately the same width as each of the two lateral areas at about their axial mid-point. The areas A and B have been found to exhibit an increase in bone density due to rheumatoid arthritis, possibly due to the formation of scarring. The excluded area is generally of lower bone density than areas A and B and is excluded to avoid diluting the effect of increasing density in areas A and B. The width of the corridor is therefore not critical but may suitably be as illustrated.

The reference region C is chosen to extend from below the regions A and B down the bone for as far as possible given the size of the CCD chip used in this example. It extends to about one half to two thirds of the way along the bone.

Figure 8:
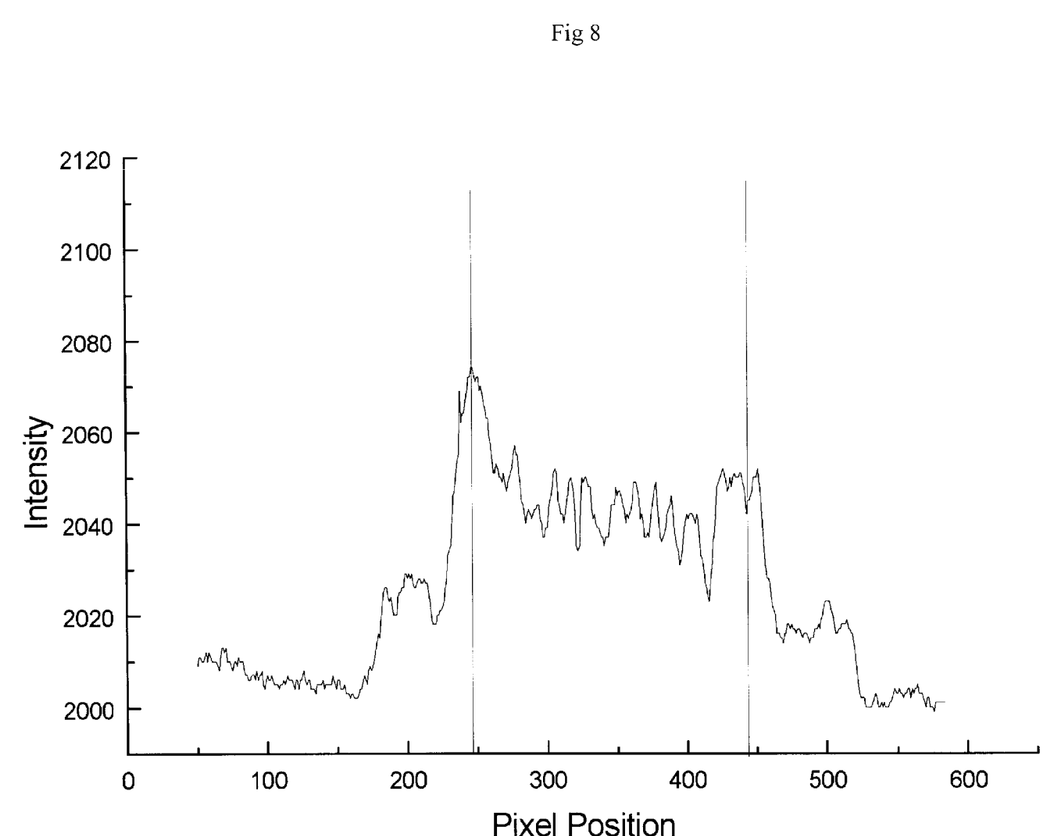
FIG. 8 shows a plot of bone density in the band between the lines VIII—VIII of FIG. 7.

The region of interest shown in FIG. 11 ("Area 21" in FIG. 12) is an approximately circular area D occupying the middle third of the bone centrally between its widest points AA and AB. From the scans shown in FIGS. 6 and 8 it can be seen that the region D is of lower bone density than the regions A and B as it lies close to the axis of the bone. However, as seen in FIG. 6; the bone density in area D is relatively high compared to other areas close to the bone axis.

In this case, the measured bone density in the region of interest is combined with that measured in a reference area labelled E in FIG. 11.

The measurements made in the region of interest and in the reference area are combined to provide a read-out of the bone density in the region of interest relative to that in the reference area or vice-versa. Alternatively, one may be subtracted from the other. Other arithmetical operations providing a relative figure may be employed.

Figure 10:
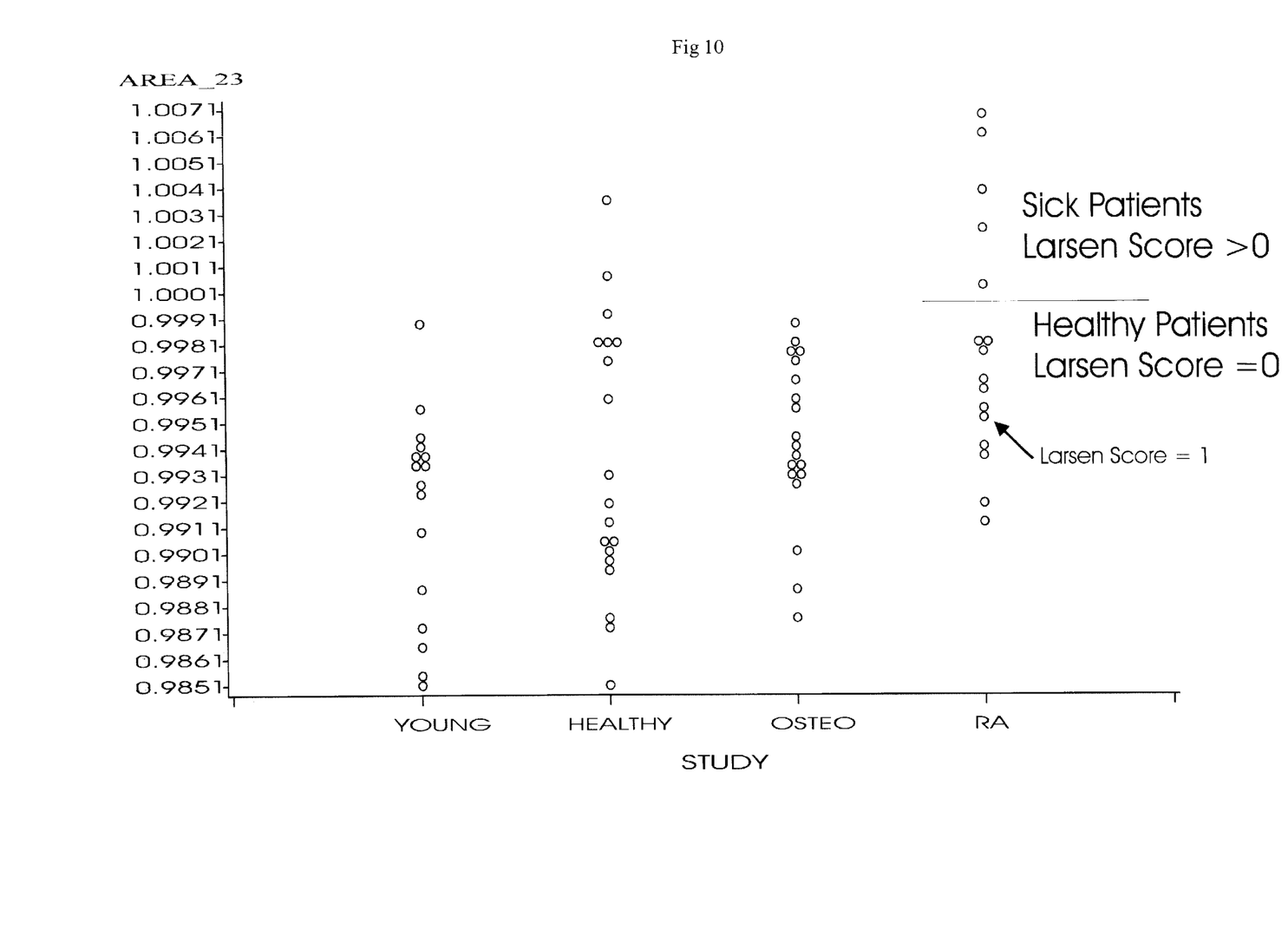
FIG. 10 shows a graphical representation of the results of a study based on measurements in the regions of interest of FIG. 9 in a number of patients.

FIG. 10 shows a graphical representation of ratios of bone density measured at A, B and C for four groups of patients. The group labelled "young" are pre-menopausal women, the group labelled "healthy," are post-menopausal, the group labelled "osteo" are post-menopausal with diagnosed osteoporosis, and the group labelled "RA" are post-menopausal with diagnosed rheumatoid arthritis. The RA group is sub-divided into two, a first sub-group having rheumatoid arthritis in the measured joint (Larsen score>0) and the other sub-group although suffering from rheumatoid arthritis are healthy in the measured joint (Larsen score>0), As can be seen, the measured ratio successfully separates the patients of the two sub-groups of RA patients to either side of a dividing line according to whether their normalised ratio is >1, except for one patient with Larsen score =1 who appears below the dividing line. The patients in the non-RA groups with few exceptions fall below the dividing line.

Figure 12:
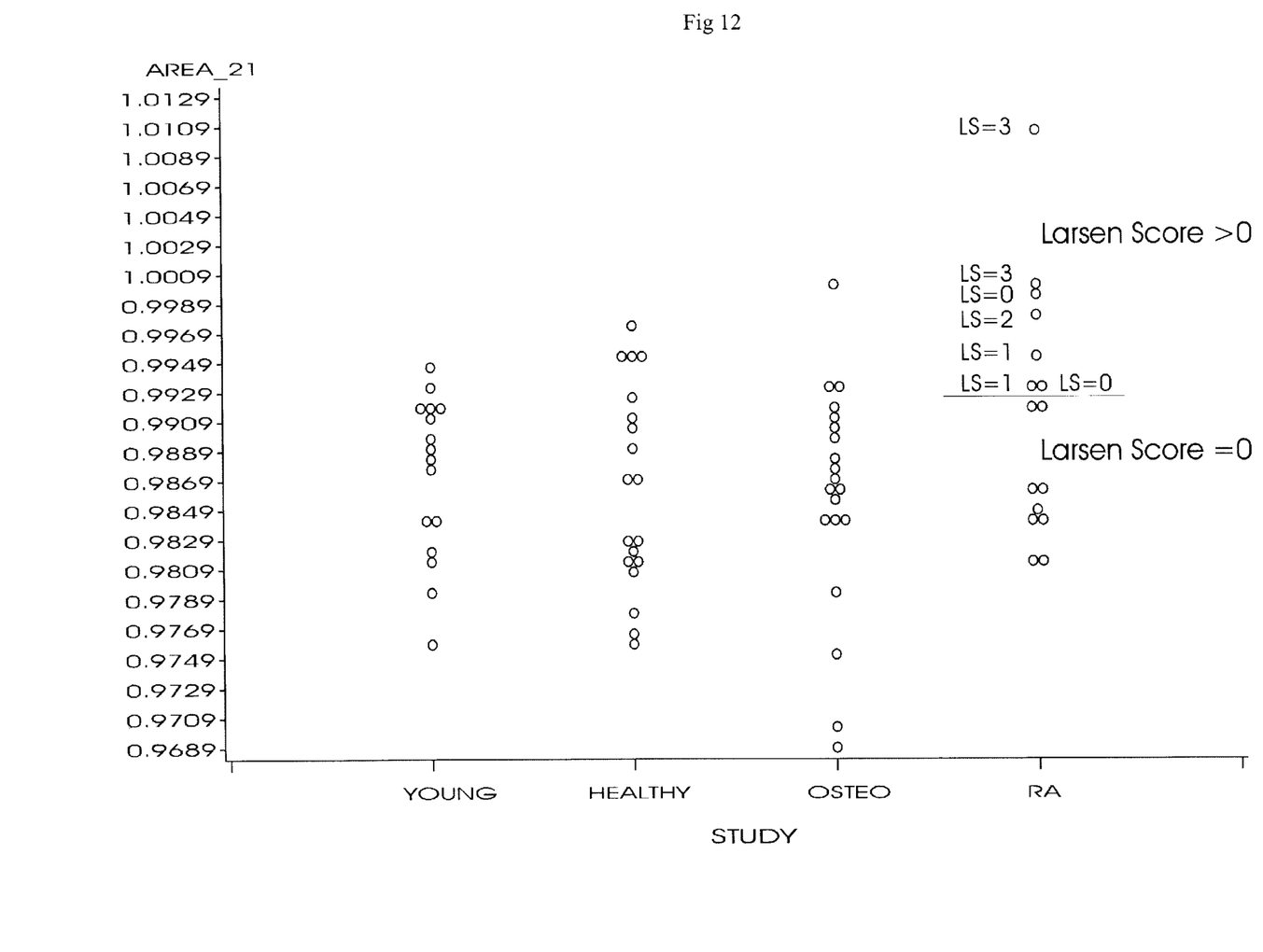
FIG. 12 shows results similar to those of FIG. 10 but based on the regions of interest of FIG. 11.

Similar results based on the regions of interest shown in FIG. 11 are shown in FIG. 12.

Although the invention has been described mainly in relation to imaging of the joints of the hand or foot, it may also be applied to other joints generally, including the shoulder, elbow or knee.

Whilst the invention has been described with reference to the specific embodiment, many modifications and variations thereof are possible within the scope of the invention. For instance, instead of deriving a relative bone density as described, it is possible to calibrate the apparatus by some alternative means such as the use of a phantom and to produce an absolute bone density reading for the area behind the end plate of the bone and/or the area further away from the joint.

The system may be used as a tool for diagnosing arthritis but also as a means of checking the effectiveness of a treatment for the disease or monitoring the progress of the disease.

Rather than making a single image, the apparatus may be such as to image the two areas separately, one may thus use a smaller imaging sensor.

The comparison made need not be between the region close to the joint and a single, selected region remote from the joint. Instead, one may measure the slope of the BMD value along the bone, associating a diagnosis of rheumatoid arthritis with a steeper slope and a healthy finger with a less steep or flat slope.

One can of course make measurements in bones associated with a number of joints, e.g. of both the hand and foot, and combine the results for a more complete and reliable picture of the patient's condition as a basis for forming a diagnosis.

What is claimed is:

1. A method for diagnostic imaging comprising producing at least one image of at least a portion of a bone involved in a potentially arthritic joint based on data reflective of bone density, said at least one image including a first region of said bone sufficiently close to said joint to be affected by an arthritic condition and a second region of said bone at least part of which is spaced from said first region, and determining bone density of said first region and the bone density of said second region to obtain a first at least one value, and making a comparison of said first at least one value with a corresponding at least one second value indicative of an arthritic condition.

2. A method as claimed in claim 1, wherein said basis for comparison is a value indicative of a rheumatoid arthritis condition.

3. A method as claimed in claim 2, wherein the bone is a bone of the hand or the foot.

4. A method as claimed in claim 3, wherein the joint is a metacarpal joint, a metatarsal joint, a finger joint or toe joint.

5. A method as claimed in any preceding claim, wherein a read out is provided of the bone density or of a bone density related value along a line axial of said bone extending from said joint.

6. A method as claimed in claim 5, wherein the slope of said value along said line is measured for diagnostic use.

7. A method as claimed in any preceding claim, wherein said region of said bone close to said joint is a region immediately behind the end plate of the bone.

8. A method as claimed in any preceding claim, wherein said region of the bone close to said joint is defined with reference to or at a location of increased bone density due to disease.

9. A method as claimed in any preceding claim, wherein said read out is of a ratio between the bone density measured at flanking regions of the bone adjacent said joint and the bone density measured in a region encompassing a substantial part of the bone excluding said flanking regions.

10. A method as claimed in any preceding claim, wherein one or both of said regions of bone are regions in which the bone has a high trabecular content.

11. A method as claimed in claim 10, wherein both said regions are close to or at the axial centre of said bone.

12. A method of obtaining data relevant to the diagnosis of arthritic conditions, comprising measuring the bone density of a portion of a bone involved in a potentially arthritic joint, said portion being adjacent the end of the bone involved in said joint, and comparing said bone density measurement with at least one value for said measurement indicative of an arthritic condition.

* * * * *